United States Patent
Heideman et al.

(10) Patent No.: US 8,254,733 B2
(45) Date of Patent: Aug. 28, 2012

(54) OPTICAL CHEMICAL DETECTOR AND METHOD

(75) Inventors: Rene Gerrit Heideman, Oldenzaal (NL); Ronald Dekker, Amersfoort (NL)

(73) Assignee: Octrolix B.V. (NL)

( * ) Notice: Subject to any disclaimer, the term of this patent is extended or adjusted under 35 U.S.C. 154(b) by 212 days.

(21) Appl. No.: 12/710,729

(22) Filed: Feb. 23, 2010

(65) Prior Publication Data
US 2010/0150496 A1  Jun. 17, 2010

Related U.S. Application Data

(63) Continuation of application No. 12/045,570, filed on Mar. 10, 2008, now Pat. No. 7,885,490.

(51) Int. Cl.
*G02B 6/00* (2006.01)
*C12Q 1/00* (2006.01)

(52) U.S. Cl. .............................. 385/12; 435/4
(58) Field of Classification Search ............ 385/12
See application file for complete search history.

(56) References Cited

U.S. PATENT DOCUMENTS

| | | | |
|---|---|---|---|
| 5,305,087 A | 4/1994 | Bernard et al. | |
| 5,312,535 A | 5/1994 | Waska et al. | |
| 5,917,188 A | 6/1999 | Atkinson et al. | |
| 6,194,900 B1 | 2/2001 | Freeman et al. | |
| 6,583,399 B1 | 6/2003 | Hunziker et al. | |
| 6,657,731 B2 | 12/2003 | Tapalian et al. | |
| 6,690,687 B2 | 2/2004 | Ksendzov et al. | |
| 6,721,053 B1 | 4/2004 | Maseeh | |
| 6,856,641 B2 | 2/2005 | Ksendzov | |
| 7,184,632 B2 | 2/2007 | de Almeida et al. | |
| 7,257,279 B2 | 8/2007 | Guo et al. | |
| 7,259,855 B2 | 8/2007 | Fan et al. | |
| 2004/0023396 A1 | 2/2004 | Boyd et al. | |
| 2005/0078731 A1 | 4/2005 | Fan et al. | |
| 2005/0162656 A1 | 7/2005 | Zhou et al. | |
| 2006/0062508 A1 | 3/2006 | Guo et al. | |
| 2006/0165342 A1 | 7/2006 | Pau et al. | |
| 2007/0147732 A1 | 6/2007 | Sanders | |
| 2007/0269901 A1 | 11/2007 | Armani et al. | |
| 2008/0265147 A1 | 10/2008 | Fan et al. | |
| 2009/0310140 A1 | 12/2009 | Smith et al. | |

FOREIGN PATENT DOCUMENTS

WO  9103728 A1  3/1991

OTHER PUBLICATIONS

Delage et al., "Label-Free Biological Sensors Based on Ring Resonators", "International Conference on Transparent Optical Networks 2008 XP-031306368", Jun. 22, 2008, pp. 25, Publisher: IEEE, Published in: US.
White et al., "Liquid-core optical ring-resonator sensors", "Optics Letters XP-001242649", May 1, 2006, pp. 1319-1321, vol. 31, No. 9, Publisher: Optical Society of America, Published in: US.

(Continued)

*Primary Examiner* — Rhonda Peace
(74) *Attorney, Agent, or Firm* — Kaplan Breyer Schwarz & Ottesen LLP

(57) ABSTRACT

An apparatus and method for optically detecting the presence of an analyte in a solution is presented. An embodiment comprises a waveguide resonator that is optically coupled to a fluid in a fluidic conduit so that the resonant wavelength of the waveguide resonator is based on the refractive index of the fluid.

22 Claims, 9 Drawing Sheets

OTHER PUBLICATIONS

Grego et al., "Wavelength interrogation of grating-based optical biosensors in the input coupler configuration", "Sensors and Actuators B—Chemical XP-022635062", Dec. 5, 2007, pp. 347-355, vol. 131, No. 2, Publisher: Elsevier B.V.

Spott, Thorsten, "EP Application No. 09003077.6 International Search Report Aug. 16, 2010", , Publisher: EPO, Published in: EP.

Peace, Rhonda S., "U.S. Appl. No. 12/045,570 Notice of Allowance-2 Sep. 27, 2010", , Publisher: USPTO, Published in: US.

Zhu et al., "Analysis of biomolecule detection with optofluidic ring resonator sensors", "Optics Express", Jul. 23, 2007, pp. 9139-9146, vol. 15, No. 15, Publisher: Optical Society of America.

Butler et al., "Capillary Electrophoresis Detector Using a Light Emitting Diode and Optical Fibres", "The Analyst", Sep. 1997, pp. 949-953, vol. 122.

Levy et al., "On-chip microfluidic tuning of an optical microring resonator", "Applied Physics Letters", 2006, No. 88, Publisher: American Institute of Physics, Published in: US.

Peace, Rhonda S., "U.S. Appl. No. 12/045,570 Office Action Jan. 8, 2010", , Publisher: USPTO, Published in: US.

Peace, Rhonda S., "U.S. Appl. No. 12/045,570 Office Action Aug. 24, 2009", , Publisher: USPTO, Published in: US.

Peace, Rhonda S., "U.S. Appl. No. 12/045,570 Notice of Allowance Mar. 31, 2010", , Publisher: USPTO, Published in: US.

Tittel et al, "Recent Advances and Applications of Mid-Infrared based Trace Gas Sensor Technology", "Proceedings of SPIE XP007918087", Feb. 7, 2008, vol. 6900.

Peace, Rhonda S., "U.S. Appl. No. 12/710,669 Notice of Allowance Nov. 16, 2011", , Publisher: USPTO, Published in: US.

Spott, Thorsten, "EP Application No. 09003077.6 Extended European Search Report Apr. 18, 2011", , Publisher: EPO, Published in: EP.

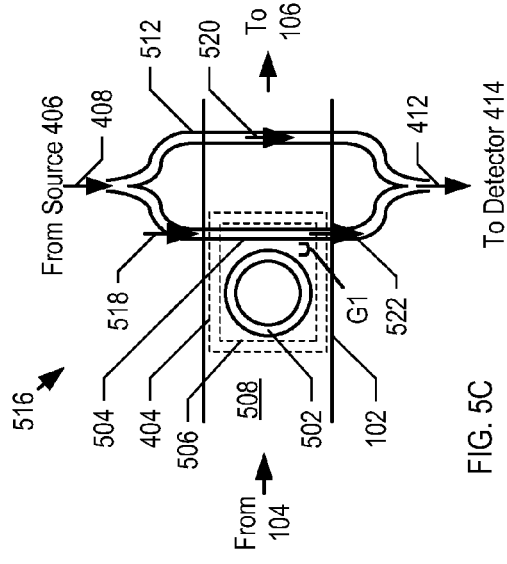
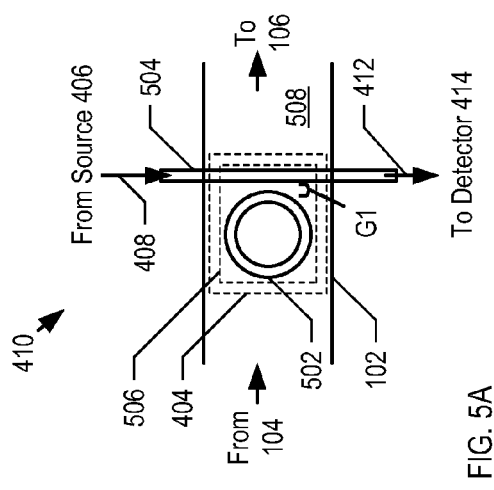
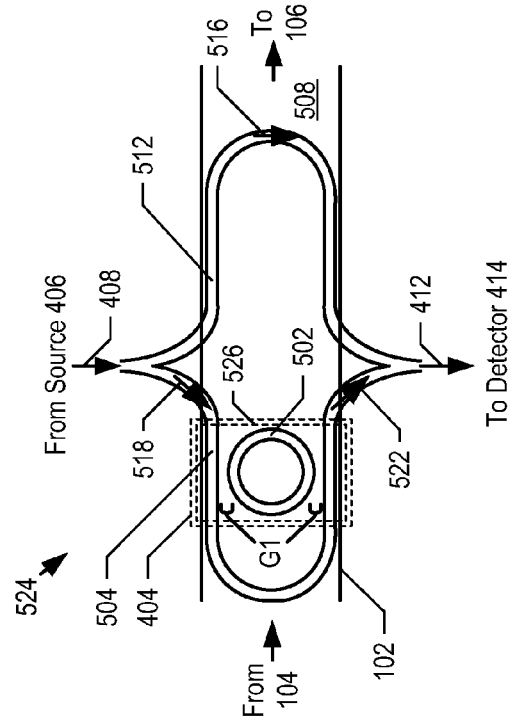
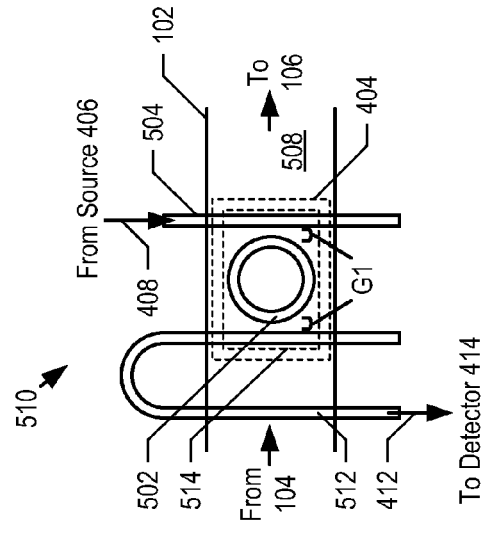

OPTICAL CHEMICAL DETECTOR AND METHOD

CROSS REFERENCE TO RELATED APPLICATIONS

This case is a continuation of co-pending U.S. patent application Ser. No. 12/045,570 filed 10 Mar. 2008, which is incorporated by reference herein.

FIELD OF THE INVENTION

The present invention relates to chemical detection in general, and, more particularly, to optical chemical detection.

BACKGROUND OF THE INVENTION

Microfluidic systems offer potential advantage in applications such as chemical synthesis, distillation, and analysis. Numerous microfluidic systems have been developed, wherein minute volumes of fluids are mixed, separated, heated, reacted, and the like. In order to control such processes, it is imperative that each chemical component be controlled. This requires, fundamentally, an ability to detect the presence of a chemical in a fluid. Further, it is advantageous to be able to monitor the chemical concentration in real-time as well.

In general, a chemical component can not, itself, be directly measured. As a result, detection methods rely on the detection of a change in a measurable property of the chemical, such as electrical conductivity, viscosity, color, absorption, refractive index, and the like. As such, chemical components are often referred to as analytes. An analyte is a substance or chemical constituent that is determined in an analytical procedure, such as a titration. For instance, in an immunoassay, the analyte may be the ligand or the binder, while in blood glucose testing, the analyte is glucose. For the purposes of this specification, including appended claims, the term analyte is used to refer to a chemical or biological component present in a carrier solution, such as a buffer solution.

There are many known methods for detecting the presence of an analyte in a fluid. These include fluorescence microscopy, visual inspection of the fluid, monitoring electrical conductivity of the fluid, and optical detection of a change in an optical property of the fluid. In most prior-art systems, however, these methods rely on the detection of a very small change in a property of the solution. To complicate matters further, these methods often provide an output signal that varies in linear fashion, commensurate with the small change in the property. As a result, the signal strength associated with the presence of the signal is often low and thus the signal-to-noise ratio of the output signal is poor. This limits the sensitivity of such detection methods.

Fluorescence microscopy offers high sensitivity detection of an analyte; however, it requires the existence of a suitable fluorescent molecule that can be attached to the analyte. In a typical fluorescence application, an analyte is selectively labeled with a fluorescent molecule called a fluorophore (e.g., green fluorescent protein (GFP), fluorescein or DyLight 488, etc.). The "tagged" specimen is illuminated with light of a specific wavelength (or wavelengths) which is absorbed by the fluorophores. The absorbed light causes them to emit light at a different color than the absorbed light. The presence of the analyte is indicated when this emitted light is detected. A fluorescence detection system normally requires a microscope, light source (e.g., a xenon arc lamp or mercury-vapor lamp), multiple color filters, and a dichroic mirror or beam-splitter (i.e., a mirror that reflects one color but not another). The filters and the dichroic elements are chosen to match the excitation and emission wavelengths of the fluorophore used to label the specimen. Although capable of high sensitivity, a fluorescence detection system is quite complicated and can be very expensive.

Other optical detection methods generally rely upon passing a light beam through the fluid and detecting a change in absorption or refractive index through detecting a change in the intensity of the light beam. There are several drawbacks to such approaches, however. First, the change in the measured optical property is typically small. In order to obtain a detectable output signal, therefore, a large amount of fluid must be interrogated. As a result, the detection region of such systems is typically large. As an analyte begins to reach the detection region, its concentration is non-uniform and initially very low. Since only a small portion of the detection region contains analyte, its effect on the entire light beam is muted. This reduces the effective chance induced by the arrival of the analyte. As the analyte continues flowing into, and fills, the detection region, the concentration level slowly builds and the output signal slowly changes until it is detectable. These factors lead to an uncertainty into the time at which the analyte has arrived. In addition, the need to interrogate a large amount of the fluid increases the cost of such a system since its overall size must be increased to accommodate the larger detection region.

Secondly, since these methods require that optical energy pass through the solution itself, they are inappropriate for use in some applications. For example, some analytes are sensitive to light and may be damaged or chemically altered when exposed to such energy.

There exists a need, therefore, for chemical detection that is highly sensitive and that can rapidly provide a discernable output signal.

SUMMARY OF THE INVENTION

The present invention enables detection of one or more analytes present in a fluid. Embodiments of the present invention are particular well-suited for use in microfluidic applications, such as lab-on-a-chip, chemical reactor on a chip, microfluidic reactors, analytic systems, capillary electrophoresis, and the like.

Embodiments of the present invention, like the prior art, provide an output signal when an optical property of a buffer solution, such as refractive index, changes due to the presence of an analyte in the solution. In the prior art, however, the output signal is a substantially linear function of the change in the optical property. As a result, a small change in the optical property is difficult to discern because it leads to only a small output signal. Prior art approaches, therefore, typically employ a large detection region so that a small change can be more easily detected.

In contrast to the prior art, the present invention a sensing element that can provide a substantially non-linear response to a change in an optical property of the buffer solution. In some embodiments, a waveguide resonator is used as the sensing element, wherein the wavelength at which the waveguide resonator is optically resonant is a function of the refractive index of the fluid at a detection region. The cladding of the waveguide resonator comprises the fluid and the resonant wavelength of the waveguide resonator, therefore, is strongly dependent upon the refractive index of the fluid. As a result, the intensity of a light signal provided to a detector by the waveguide resonator is a highly non-linear function of the refractive index of the fluid. In addition, in some embodiments, the sensing element is approximately the same size as the analyte sample, enabling a rapid and definitive output in response to the presence of the analyte in the detection region.

In some embodiments, the present invention provides a light signal to a detector, wherein the presence of an analyte in a fluid at a detection region is indicated by the intensity of the light signal. In some embodiments, a waveguide resonator receives light, having a first wavelength, from a source. The waveguide resonator then provides an output light signal, having the first wavelength, to a detector, wherein the intensity of the output light signal is based on the optical resonance of the waveguide resonator. For example, in some embodiments, the waveguide resonator provides a low intensity output light signal when it is optically resonant at the first wavelength, but a high intensity output light signal when it is non-optically resonant. In some embodiments, a waveguide resonator is optically resonant at the first wavelength when the fluid in the detection region is analyte-free. In some embodiments, a waveguide resonator is optically resonant at the first wavelength when the fluid in the detection region comprises an analyte.

In some embodiments, a waveguide resonator is arranged in an interferometer arrangement, and input light split into a first signal in a first waveguide that is included in a waveguide resonator, and a second signal that is conveyed through a second waveguide that is not included in a waveguide resonator. The first and second signals are combined into an output light signal whose intensity is based on the relative phases of the first and second signals when combined.

In some embodiments, a waveguide resonator is arranged in a waveguide resonator mirror configuration that forms an external mirror of an external cavity laser. The intensity and wavelength of the output of this external cavity mirror are based on the refractive index of a fluid in a detection region. In some embodiments, the concentration of an analyte in the fluid is determined, based upon a shift in the resonant wavelength of the waveguide resonator.

An embodiment of the present invention comprises a fluidic conduit for conveying a fluid, wherein the fluidic conduit comprises a first region; and a first waveguide resonator, wherein the first waveguide resonator is optically resonant for a first spectral component when the fluid in the first region has a first refractive index, and wherein the first waveguide resonator is optically resonant for a second spectral component when the fluid in the first region has a second refractive index.

BRIEF DESCRIPTION OF THE DRAWINGS

FIG. 5A depicts a schematic diagram of details of sensor element 410 in accordance with the illustrative embodiment of the present invention.

FIG. 5B depicts a schematic diagram of details of a sensor element in accordance with a first alternative embodiment of the present invention.

FIG. 5C depicts a schematic drawing of details of a sensor element in accordance with a second alternative embodiment of the present invention.

FIG. 5D depicts a schematic diagram of details of a sensor element in accordance with a third alternative embodiment of the present invention.

DETAILED DESCRIPTION

The terms that appear below are provided with the following explicit definitions for use in understanding the specification and interpreting the appended claims:

Free spectral range is the distance (in frequency space) between adjacent transmission peaks.

Spectral component refers to optical energy characterized by a particular wavelength. In the context of real-world technological applications, as opposed to a theoretical discussion, a spectral component will never actually be characterized by only a single wavelength. Rather, the electromagnetic spectrum of the spectral component will include a plurality of wavelengths that are centered about a predominant, primary or center wavelength.

Evanescent-coupling relation refers to a relationship between two or more elements, typically optical waveguides, wherein an optical signal traveling through one of the elements is capable of coupling at least some of its optical energy, via evanescent field coupling, into the other element.

Other definitions may appear throughout this specification as appropriate.

The present invention provides detection of a chemical species or biological agent in a solution contained in a microfluidic system, such as in a lab-on-a-chip application. Although the illustrative embodiment described herein comprises a capillary electrophoresis system, it will be clear to those skilled in the art, how to make and use alternative embodiments of the present invention that comprise microfluidic systems other than capillary electrophoresis systems, such as lab-on-a-chip, chemical reactor on a chip, microfluidic reactors, analytic systems, capillary electrophoresis, and the like.

Figure 1:
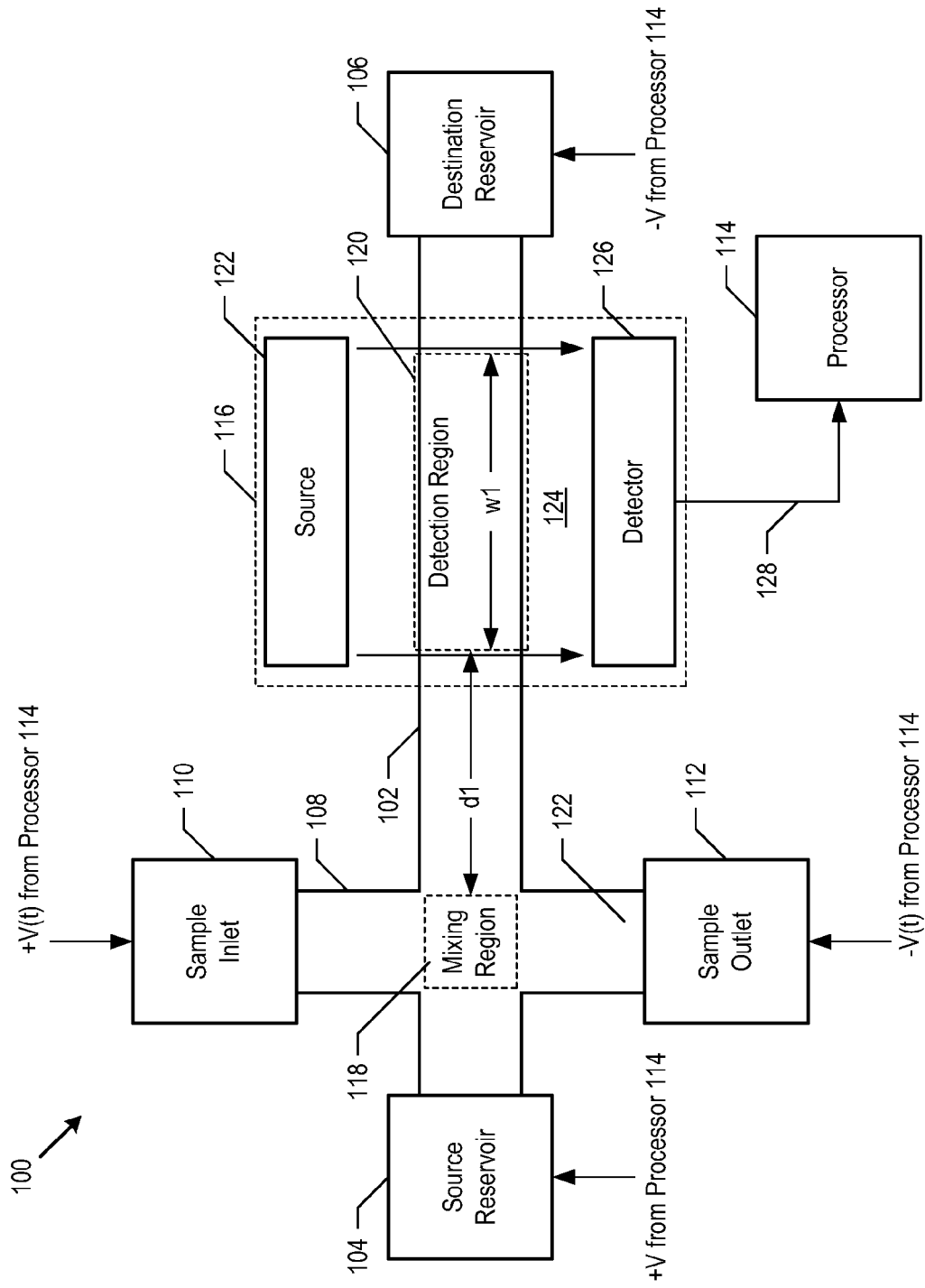
FIG. 1 depicts a schematic diagram of details of a capillary electrophoresis system in accordance with the prior art.

FIG. 1 depicts a schematic diagram of details of a capillary electrophoresis system (hereinafter, CE system) in accordance with the prior art. CE system 100 comprises flow channel 102, source reservoir 104, destination reservoir 106, sample channel 108, sample inlet 110, sample outlet 112, processor 114, and sensor 116.

Capillary electrophoresis is a well-known technique for analyzing samples of chemicals, cells, and biological matter. In operation, a buffer solution flows through flow channel 102 from source reservoir 104 to destination reservoir 106. Processor 114 applies a steady-state high voltage, V, typically in the range of 10-30 kilovolts, between source reservoir 104 and destination reservoir 106. This high voltage induces electro-osmotic flow of the buffer solution along flow channel 102 from source reservoir 104 to destination reservoir 106. In some CE systems, flow of buffer solution through flow channel 102 is induced by applying a pressure differential between source reservoir 104 to destination reservoir 106.

At time t(0), processor 114 applies a voltage pulse V(t) between sample inlet 110 and sample outlet 112. This applied voltage induces a charge of sample solution to be injected into the buffer solution at mixing region 118, where it mixes with the buffer solution.

As the charge of sample solution flows through the length, d1, of flow channel 102, the sample solution disassociates into its constituent analytes. The analytes separate because each analyte travels through flow channel 102 at a rate that is based on its individual physical properties.

Detector 116 is an optical detector for detecting the presence of an analyte in the buffer solution at detection region 120. In some CE systems, simple visual inspection is used to detect the presence of an analyte. In other CE systems, non-optical detection means, such as electrical conductivity sensors, are used to detect an analyte.

Detector 116 generates a signal in response to a change in the optical characteristics of the solution in detection region 120, wherein the change is due to the presence of an analyte in the buffer solution. Prior to any of the constituent analytes of the sample solution reaching it, detection region 120 contains only pure buffer solution. As a result, optical signal 124 is received by photodetector 126 at a steady-state intensity. The intensity of optical signal at photodetector 126 is based on the absorption coefficient and refractive index of the pure buffer solution. Prior to the arrival of an analyte at detection region 120, therefore, photodetector 126 provides a steady-state output signal 128 to processor 114.

At time t(1), a first analyte reaches detection region 120, which causes a change in the absorption coefficient and/or refractive index of the solution. This causes a change in the optical power received by photodetector 126 and a corresponding change in output signal 128. As the first analyte clears detection region 120, output signal 128 returns to its prior steady-state level. This process repeats at time t(2) for a second analyte, time t(3) for a third analyte, and so on.

Processor 114 receives output signal 128 and determines the time between sample injection, t(0) and the time each analyte was detected in detection region 120 (i.e., t(1), t(2), etc.). Processor 114 then derives an identity for each analyte based on this time differential and the distance, d1, between mixing region 118 and detection region 120 (i.e., t(1)-t(0), t(2)-t(0), etc.), and the geometry of the flow channel.

While known optical detectors, such as detector 116, provide a means of analyte detection, they do have several drawbacks. First, a change in the optical properties of the solution in detection region 120 typically induces only a small change in optical beam 124 since the optical beam passes through only a very small amount of solution. In order to achieve a detectable change in received optical power, therefore, the width, w1, of the detection region is made large. The interaction length of detection region 120 is directly proportional to its width, w1.

A wide detection region, however, leads to uncertainty in analyte arrival time. As the analyte first arrives at detection region 120, the majority of the detection region still contains pure buffer solution. As a result, a change in the optical properties of the solution in the detection region is difficult to detect. As the analyte concentration in the detection region increases to a sufficient level, a change in the intensity of optical signal 124 will be detected. This change, however, will occur relatively slowly. In addition, a wide detection region leads to an uncertainty in the distance the analyte has traveled when it is detected. As a result, it can be difficult to correctly identify an analyte with prior art optical detection methods.

In addition, a wide detection region increases the overall size of the microfluidic chip, which leads to increased cost. Further, additional optics are often required, such as a cylindrical lens to expand optical beam 124 in one dimension while constraining it in another dimension. This also leads to additional system cost and complexity.

In contrast to prior art detection methods, the present invention provides a more definitive detection of the presence of analyte in a solution. The present invention comprises a waveguide resonator that is integrated with the flow channel to form a small detection region. The present invention relies on the fact that waveguide resonator has a non-linear response. As a result, a small change of refractive index of the solution in the detection region can cause a large change in resonant characteristics of the waveguide resonator.

Since the effective interaction between the solution and the optical signal is magnified, as compared to prior art approaches, the detection region can be very small. In fact, in some embodiments, the detection region needs to be no larger than the size of the waveguide resonator itself. In addition, some embodiments of the present invention comprise waveguides that are characterized by an inner core of silicon dioxide and an outer core of silicon nitride. This waveguide core structure advantageously enables the use of a thin cladding for waveguides of the waveguide resonator. Thus, optical coupling between the solution and the waveguide resonator is more easily enabled, as described below and with reference to FIG. 5A.

Waveguide Resonator Operation

A waveguide resonator comprises an optically resonant element and one, or more typically two, linear waveguides. The linear waveguides are usually termed "port waveguides" or "bus waveguides;" the latter phrase will be used herein. In a disc resonator, the optically resonant element is a solid disc of optical material. In a ring resonator, the optically resonant element is a closed-loop of waveguide material (hereinafter referred to as a "loop waveguide"). The embodiments described herein all comprise ring resonators. It will be clear to one of ordinary skill in the art, however, after reading this specification, how to make and use alternative embodiments of the present invention that comprise one or more disc resonators.

Certain frequencies of light resonate within the loop waveguide and, as a consequence of resonator geometry, resonant light couples between the loop waveguide and the bus waveguides. A ring resonator, therefore, effectively functions as a highly-selective wavelength-dependent optical coupler.

In most implementations, light energy is coupled into and out of the micro-resonator's loop waveguide via evanescent field coupling. An evanescent optical field is the portion of the optical field of guided light that extends beyond the physical surface of a waveguide core (e.g., the portion of the optical field that extends into the waveguide's cladding). The strength and extent of the evanescent optical field beyond the waveguide core is a function of the contrast between the refractive index of the core and cladding layers, and the refractive index of the cladding layer itself. The ability for an evanescent optical field to couple from one waveguide into another is a function of the proximity of the two waveguides, the refractive index and thickness of the waveguides' cladding layers, the refractive index of any material between the claddings of the waveguides, and the wavelength of the light.

In a conventional ring resonator, evanescent coupling between a loop waveguide and bus waveguide is achieved by placing them in close proximity. Light propagating in the bus waveguide that is at the resonant wavelength is coupled from the bus waveguide to the loop waveguide. Light propagating in the bus waveguide that is off-resonance (i.e., not at the resonance wavelength) bypasses the loop waveguide and continues to propagate down the bus waveguide.

In the present invention, evanescent coupling between a bus waveguide and a loop waveguide is enabled when the claddings of the loop waveguide and bus waveguide are in contact with a solution having an appropriate refractive index. The optical properties of the solution are incorporated into the optical characteristics of the waveguide cladding. As a result, the refractive index of the solution has a dramatic impact on the light guiding capability of the waveguides. In effect, the solution becomes part of the claddings of the loop and bus waveguides. The refractive index of the solution, therefore, determines for what wavelengths the evanescent optical field couples between the loop waveguide and the bus waveguide (i.e., for what wavelengths the waveguide resonator is optically resonant).

The shape of the "loop" of the closed-loop waveguide is typically circular, oval or elliptical, but can alternatively have an arbitrarily curved circumference in the form of a distorted ring. The loop waveguide used in conjunction with the present invention will typically have a circular shape to minimize its size, but any of the aforementioned geometries can suitably be used.

Ring resonators are typically fabricated in one of two arrangements: "laterally coupled" or "vertically-coupled." In a laterally coupled ring resonator, the bus waveguides are in the plane of the loop waveguide. In a vertically-coupled resonator, the bus waveguides are situated either both above, both below, or one above and one below the loop waveguide. Each of these two basic arrangements has well-understood advantages and drawbacks. Either arrangement can be used in conjunction with the present invention.

Figure 2:
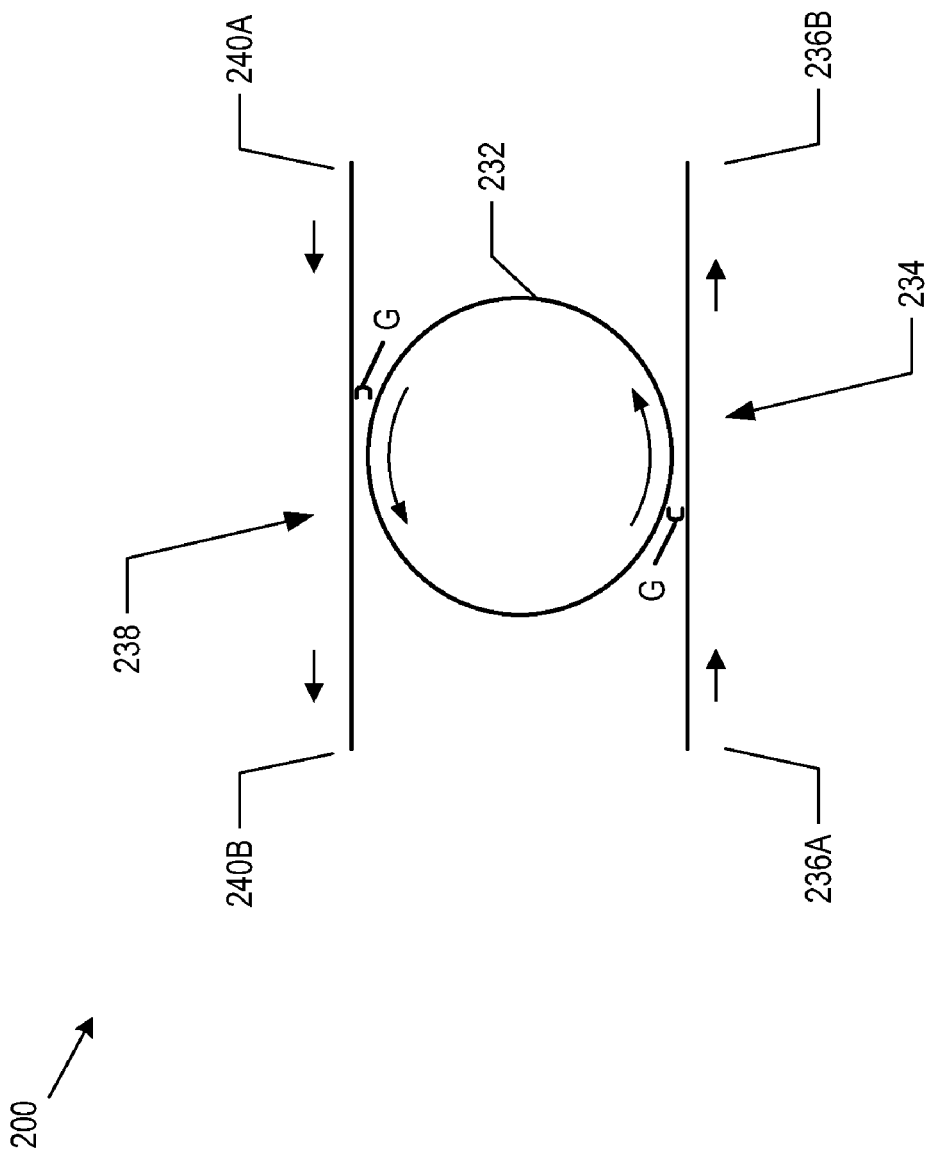
FIG. 2 depicts a schematic representation of a typical prior-art laterally coupled ring resonator for coupling light from a first bus waveguide into a second bus waveguide.

FIG. 2 depicts a schematic representation of a typical prior-art laterally coupled ring resonator for coupling light from a first bus waveguide into a second bus waveguide. Ring resonator 200 comprises closed-loop waveguide 232 and two bus waveguides 234 and 238. Ring resonator 200 has four ports: input port 236A and pass port 236B defined on bus waveguide 234 and add port 240A and drop port 240B defined on bus waveguide 238.

A portion of each of bus waveguides 234 and 238 is adjacent and tangential (i.e., in the direction of a tangent) to loop waveguide 232. At this portion of the bus waveguides, they are separated from loop waveguide 232 by gap G. This gap is small enough to permit evanescent field coupling, as previously discussed.

In some alternative implementations (not depicted), respective portions of each of waveguides 234 and 238 that are adjacent to loop waveguide 232 are not tangential thereto; rather, they curve around a portion of loop waveguide 232 to increase the interaction length (for coupling). In some further implementations, a vertically-coupled ring resonator includes bus waveguides that are disposed orthogonally to one another (see, e.g., U.S. Pat. No. 6,411,752).

Certain wavelengths of light resonate within loop waveguide 232 as a function of loop characteristics. Consider a multi-wavelength optical signal propagating in bus waveguide 234 past input port 236A. Light that has a wavelength that is off-resonance with loop waveguide 232 bypasses the loop and is output from pass port 236B of bus waveguide 234. Light that has a wavelength that is on-resonance couples to loop waveguide 232 via evanescent field coupling. As used in this specification and the appended claims, when "light" or a "spectral component" is described as being "off-resonance," it means that the wavelength of the light or spectral component is different from a resonant wavelength of loop waveguide 232. Similarly, when light or a spectral component is described as being "on-resonance," it means that the wavelength of the light or spectral component is the same as a resonant wavelength of loop waveguide 232.

The on-resonance light that is coupled from bus waveguide 234 propagates in loop waveguide 232 and couples to bus waveguide 238 via evanescent field coupling. The light that is coupled into bus waveguide 238 propagates in a direction opposite to the light traveling in bus waveguide 234 due to the respective orientations of the various waveguides. As a consequence, the resonant light coupled to bus waveguide 238 from bus waveguide 234 via loop waveguide 232 will be output from drop port 240B. This resonant light will be joined by off-resonance light that propagates along waveguide 238 from add port 240A.

In analogous fashion, on-resonance light traveling in bus waveguide 238 via add-port 240A couples to loop waveguide 232. That light couples to bus waveguide 234 and propagates through pass-port 236B, along with off-resonant light from input port 236A. In the arrangement that is depicted in FIG. 2, ring resonator 200 is operated so that light propagates unidirectionally—in this example in a counterclockwise direction—through loop waveguide 232.

Figure 3:
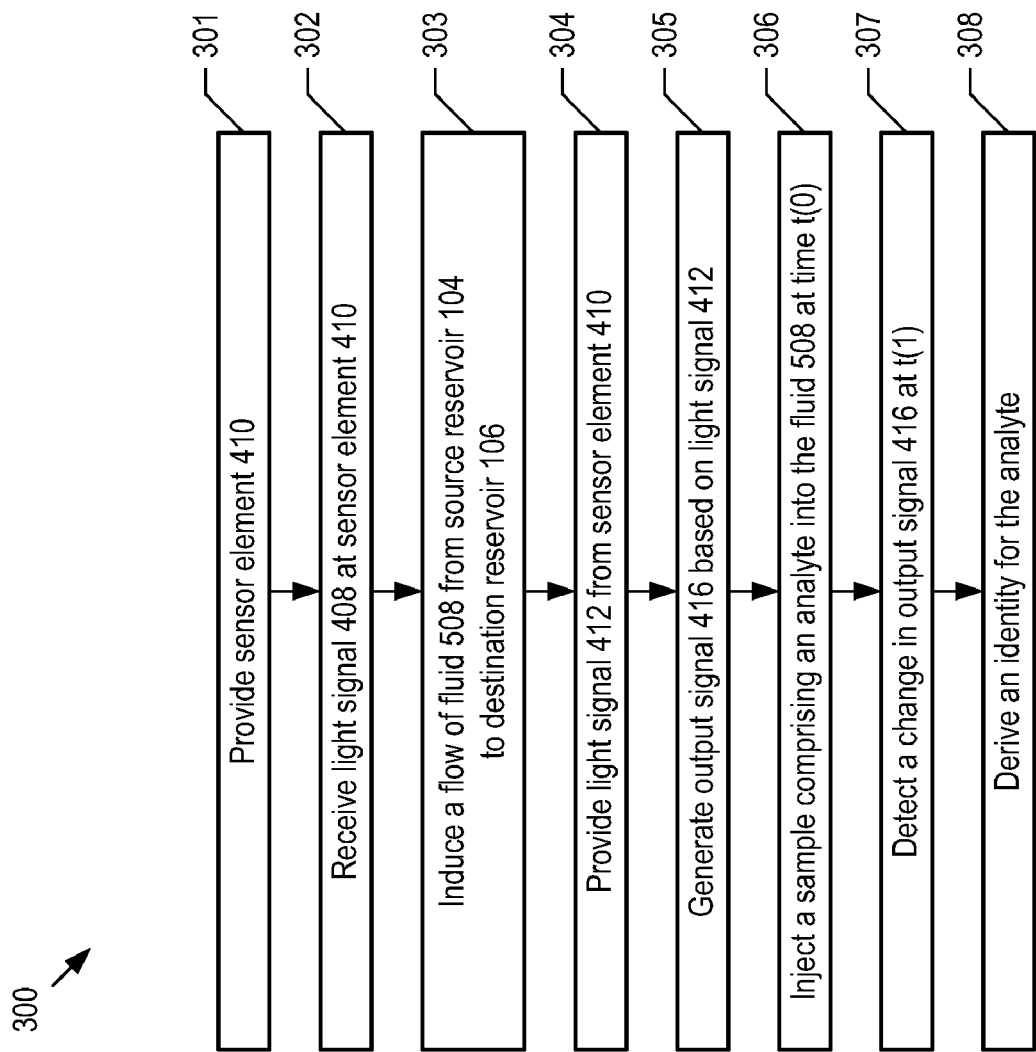
FIG. 3 depicts a method for detecting the presence of an analyte in a solution in accordance with an illustrative embodiment of the present invention.

FIG. 3 depicts a method for detecting the presence of an analyte in a solution in accordance with an illustrative embodiment of the present invention. Method 300 comprises operations for performing capillary electrophoresis. It will be clear to one skilled in the art, after reading this specification, that capillary electrophoresis is merely one application for which the present invention is suitable. Method 300 is described below with additional reference to FIGS. 4, 5A, and 6.

Figure 4:
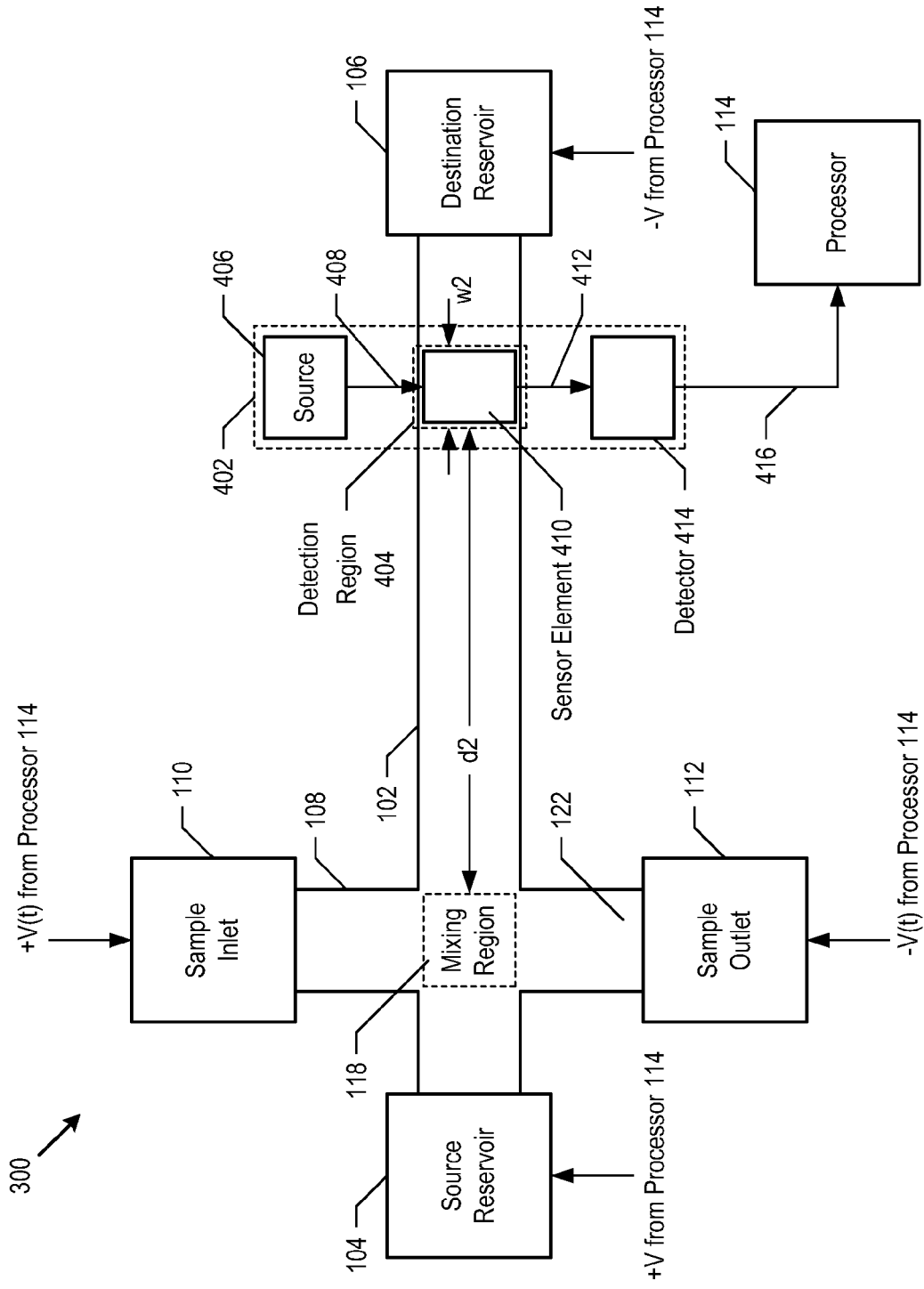
FIG. 4 depicts a schematic diagram of details of a capillary electrophoresis system in accordance with the illustrative embodiment of the present invention.

FIG. 4 depicts a schematic diagram of details of a capillary electrophoresis system in accordance with the illustrative embodiment of the present invention. CE system 400 comprises flow channel 102, source reservoir 104, destination reservoir 106, sample channel 108, sample inlet 110, sample outlet 112, processor 114, and sensor 302.

Method 300 begins with operation 301, wherein sensor element 410 is provided.

At operation 302, sensor element 410 receives light signal 408 from source 406.

Source 406 is a source of substantially monochromatic light that is centered at a wavelength of approximately 850 nm, in well-known fashion. In some embodiments, source 406 emits light centered at a wavelength different than 850 nm. Other common suitable wavelengths include 633 nm, 670 nm, 780 nm, wavelengths within the range of 1400 nm to 1650 nm, wavelengths within the range of 1250 nm to 1380 nm, and so forth. It will be clear to those skilled in the art, however, that the design of closed-loop waveguide 502 and bus waveguide 504 is dependent upon the wavelength of light emitted by source 406. Devices suitable for use in source 406 include, without limitation, semiconductor lasers, vertical-cavity surface emitting lasers (VCSELs), gas lasers, light emitting diodes, and the like. It will be clear to one skilled in the art how to make and use source 406.

FIG. 5A depicts a schematic diagram of details of sensor element 410 in accordance with the illustrative embodiment of the present invention. Sensor element 410 comprises closed-loop waveguide 502 and bus waveguide 504. Closed-loop waveguide 502 and bus waveguide 504 collectively define waveguide resonator 506. Although in the illustrative embodiment, waveguide resonator 506 is a laterally-coupled ring resonator, it will be clear to one skilled in the art, after reading this specification, how to make and use alternative embodiments of the present invention wherein waveguide resonator 506 is a vertically coupled ring resonator, a laterally coupled disc resonator, or a vertically coupled disc resonator.

Closed-loop waveguide 502 is a ring of waveguide that is formed over flow channel 102. As a result, fluid 508 in detection region 404 of flow channel 102 optically couples with the cladding of closed-loop waveguide 502. In the illustrative embodiment, closed-loop waveguide 502 has a diameter of approximately 50 microns. In some embodiments, the diameter of closed-loop waveguide 502 is within the range of approximately 15 microns to approximately 250 microns. In most applications, the desired diameter of closed-loop waveguide 502 is dictated by the size of flow channel 102 and the desired free-spectral range (i.e., the distance (in frequency space) between adjacent transmission peaks) of the waveguide resonator. It will be apparent to one of ordinary skill in the art that the free-spectral range of ring resonator 502 is inversely proportional to its diameter.

Bus waveguide 504 is a waveguide formed in close proximity to closed-loop waveguide 502. Closed-loop waveguide 502 is formed over flow channel 102 so that fluid 508 in detection region 404 of flow channel 102 optically couples with the cladding of closed-loop waveguide 502.

In some embodiments, closed-loop waveguide 502 and a portion of bus waveguide 504 are formed in flow channel 102.

Bus waveguide 504 and closed-loop waveguide 502 are separated by gap G1. In the illustrative embodiment, gap G1 is approximately 50 nanometers (nm). In some embodiments, gap G1 is within the range of approximately 10 nanometers (nm) to approximately 1 micron. The size of gap G1 is selected to enable a desired coupling ratio between closed-loop waveguide 502 and bus waveguide 504.

When fluid 508 is present in detection region 404, the fluid constitutes a portion of the cladding layers for each of closed loop waveguide 502 and bus waveguide 504. As a result, the refractive index of the fluid affects the wavelengths at which waveguide resonator 506 is optically resonant. As a result, gap G1 is selected to provide a first desired evanescent coupling ratio between closed-loop waveguide 502 and bus waveguide 504, for light having a wavelength of 850 nm, when fluid 508 is in detection region 404 is analyte-free. Alternatively, gap G1 is selected to provide a second desired evanescent coupling ratio, for light having a wavelength of 850 nm, when fluid 508 is detection region 404 comprises an analyte.

Although compatible with virtually any waveguide technology, ring resonator 502 and bus waveguide 504 are preferably formed using a waveguide technology that comprises a composite core—specifically, an inner core of silicon dioxide and an outer core of silicon nitride. Examples of suitable composite-core waveguides are described in detail in U.S. Pat. No. 7,146,087, issued Dec. 6, 2006, which is included herein by reference in its entirety. Such composite-core waveguides enable a more effective coupling of fluid 508 and their cladding layers, since their cladding layers are typically much thinner than those of more conventional waveguide technologies. As a result, waveguide resonators formed using a composite-core waveguide technology can exhibit a stronger resonant characteristic dependency on the refractive index of fluid 508 than those formed using a conventional waveguide technology.

At operation 303, flow channel 102 is filled with fluid 508, which comprises a pure buffer solution, typically a saline solution. Processor 114 then applies a high voltage between source reservoir 104 and destination reservoir 106 to induce a flow of fluid 508 between them. In some embodiments, the flow of fluid 508 is induced by another means, such as pressure, capillary action, or siphoning.

Processor 114 is a general purpose logic processor, which is also capable of controlling voltages applied to source reservoir 104, destination reservoir 106, sample inlet 110, and sample output 112. Processor 114 is also configured to receive output signal 416 from detector 414 and derive an identity of an analyte. It will be clear to those skilled in the art, after reading this specification, how to make and use processor 114.

At operation 304, light signal 412 is provided to detector 414 from sensor element 410.

The ratio of the intensity of light signal 412 to the intensity of light signal 408 is a function of the coupling ratio between closed-loop waveguide 502 and bus waveguide 504. As discussed above, and with respect to FIG. 5A, this coupling ratio is a function of the refractive index of fluid 508 in detection region 414. When fluid 508 is analyte-free (i.e., it is pure buffer solution), it has a first refractive index. When fluid 508 comprises an analyte, it has a second refractive index.

In the illustrative embodiment, when fluid 508 in detection region 404 is analyte free, waveguide resonator 506 is dimensioned and arranged to be "on-resonance" for light having a wavelength of 850 nm. The term "on-resonance" means that closed-loop waveguide 502 and bus waveguide 504 are in an evanescent coupling relation. In other words, optical energy in bus waveguide 504 couples into closed-loop waveguide 502 through gap G1.

Alternatively, when fluid 508 in detection region 404 comprises an analyte, waveguide resonator 506 is no longer on-resonance, but is instead "off-resonance" for light having a wavelength of 850 nm. The term "off-resonance" means that closed-loop waveguide 502 and bus waveguide 504 are in a substantially non-evanescent coupling relation. In other words, most or all of the optical energy in light signal 408 passes by closed-loop waveguide 502 and is therefore contained in light signal 412.

At operation 305, detector 414 provides output signal 416, which is based on light signal 412, to processor 114.

At operation 306, processor 114 applies a voltage pulse between sample inlet 110 and sample outlet 112. This applied voltage induces a charge of sample solution to be injected into fluid 508 at mixing region 118, where it mixes with the buffer solution. The charge of sample solution is injected into fluid 508 at time t(0). The sample solution comprises a mixture of a first analyte and a second analyte.

As fluid 508 flows from source reservoir 104 to destination reservoir 106, it carries the charge of sample solution along flow channel 102 for distance d2 (i.e., from mixing region 118 to detection region 404). As the charge of sample solution moves along distance d2, it disassociates into its constituent parts of the first analyte and second analyte. Each analyte moves along flow channel 102 at a rate that is a function of its unique electrophoretic mobility. Electrophoretic mobility is proportional to the ionic charge of an analyte and inversely proportional to frictional forces present in the buffer solution. When two analytes in a sample have different charges or experience different frictional forces, they will separate from one another as they migrate through a buffer solution. The frictional forces experienced by an analyte ion depend on the viscosity of the medium and the size and shape of the ion.

Figure 6:
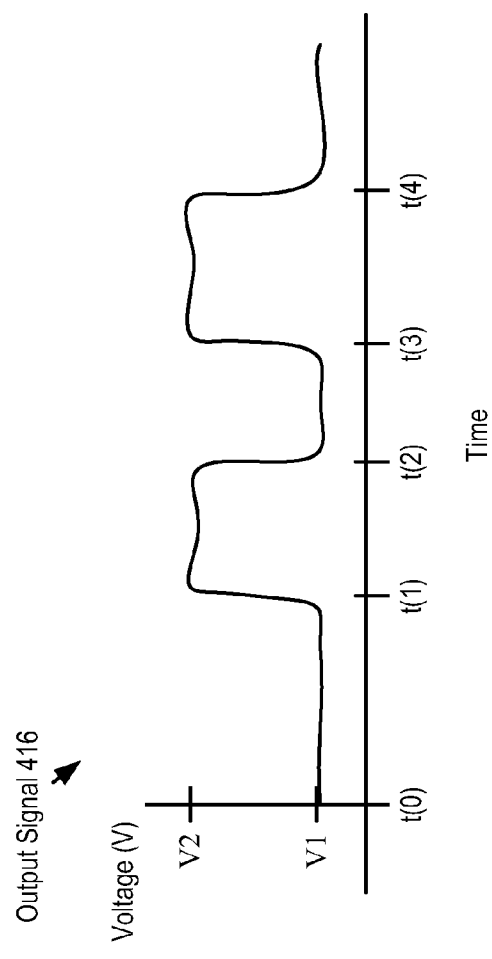
FIG. 6 depicts a plot of an output signal from sensor element 410 in accordance with the illustrative embodiment of the present invention.

At operation 307, processor 114 detects a change in output signal 416 at time t(1), due to the arrival of the first analyte at detection region 404. A representation of output signal 416 is depicted in FIG. 6.

During the time between t(0) and t(1), fluid 508 in detection region 414 is pure buffer solution and waveguide resonator 506 is on-resonance. As a result, light is coupled from bus waveguide 504 into closed-loop waveguide 502. As light travels around closed-loop waveguide 502, optical energy is lost through attenuation typically associated with propagation in any surface waveguide technology. As a result, the intensity of light signal 412 is reduced from that of light signal 408. During this time period, output signal 416 is at voltage level V1.

Due to the arrival of the first analyte at time t(1), the refractive index of fluid 508 in detection region 404 changes to its second refractive index. As a result, waveguide resonator 506 becomes off-resonance and light no longer couples from bus waveguide 504 into closed-loop waveguide 502. All of the optical energy of light signal 408 is then present in light signal 412, since there is no attenuation due to propagation in closed-loop waveguide 502. Output signal 416, therefore, increases from voltage level V1 to voltage level V2.

As fluid 508 continues to flow through flow channel 102, the first analyte becomes depleted from detection region 404 at time t(2). At this point, the refractive index of fluid 508 returns to its first refractive index. Optical energy is again coupled from bus waveguide 504 into closed-loop waveguide 502, and output signal 416 returns to voltage level V1.

With continuing flow of fluid 508, the second analyte arrives at detection region 404 at time t(3). As with the arrival of the first analyte, waveguide resonator 506 again becomes off-resonance and output signal 416 returns to voltage level V2.

At time t(4), the second analyte becomes depleted from detection region 404 and output signal 416 returns to voltage level V1.

It should be noted that differentiation of the first analyte from the second analyte is dependent upon there being a physical separation between them in fluid 508. Since, as discussed above, each analyte migrates at a rate dependent upon its unique characteristics; their physical separation will increase with longer migration distance. The present invention, therefore, enables improved analytical performance for a CE system by virtue of its smaller detection region and commensurate longer separation distance, d2.

It should also be noted that the index of refraction of fluid 508 is a function of the concentration of analyte in the fluid. The present invention affords further advantage over the prior art, therefore, since the size of sensor element can be approximately the same size as that of the charge of sample solution to be detected. As a result of the closely matched sizes, as a charge of analyte reaches detection region 404, the change in refractive index is more abrupt and more easily detected using embodiments in accordance with the present invention.

It will be clear to those skilled in the art that the present invention is suitable for analyzing samples having any number of analytes.

At operation 308, processor 114 derives an identity for the first analyte and the second analyte based on their migration times, the flow rate of fluid 508, and the geometry of flow channel 102.

FIG. 5B depicts a schematic diagram of details of a sensor element in accordance with a first alternative embodiment of the present invention. Sensor element 510 comprises closed-loop waveguide 502, bus waveguide 504, and bus waveguide 512. Closed-loop waveguide 502, bus waveguide 504, and bus waveguide 512 collectively define waveguide resonator 514.

Bus waveguide 512 is analogous to bus waveguide 504, and is separated from closed-loop waveguide 502 by gap G1.

In operation, when fluid 508 in detection region 404 is pure buffer solution, waveguide resonator 514 is on-resonance for light having a wavelength of 850 nm. As a result, optical energy will couple from bus waveguide 512 to bus waveguide 504 through closed-loop waveguide 502. While fluid 508 in detection region 404 is analyte-free, therefore, light signal 412 will have a high intensity and output signal 416 will have a high voltage level.

When fluid 508 in detection region 404 comprises an analyte, however, the refractive index of fluid 508 will change and waveguide resonator 514 will be off-resonance for light having a wavelength of 850 nm. As a result, little or no optical energy will couple from bus waveguide 512 to bus waveguide 504 through closed-loop waveguide 502. While fluid 508 in detection region 404 comprises an analyte, therefore, light signal 412 will have a low intensity and output signal 416 will be at a low voltage level.

FIG. 5C depicts a schematic drawing of details of a sensor element in accordance with a second alternative embodiment of the present invention. Sensor element 516 comprises waveguide resonator 506 and bus waveguide 512. Waveguide resonator 506 and bus waveguide 512 are arranged in an interferometer arrangement.

In operation, light signal 408 is distributed into light signals 518 and 520 in bus waveguides 504 and 512, respectively. When fluid 508 in detection region 404 is pure buffer solution, waveguide resonator 506 is on-resonance for light having a wavelength of 850 nm. As a result, light signal 518 will couple from bus waveguide 504 into closed-loop waveguide 502. This causes a phase delay on light signal 522. Light signal 522 and light signal 520 are combined into light signal 412. Due to the phase delay induced on light signal 522 by waveguide resonator 506, however, light signals 522 and 520 destructively interfere. This reduces the intensity of light signal 412. While fluid 508 in detection region 404 is analyte-free, therefore, light signal 412 will have a low intensity and output signal 416 will be at a low voltage level.

When fluid 508 in detection region 404 comprises an analyte, however, the refractive index of fluid 508 will change and waveguide resonator 506 will become off-resonance for light having a wavelength of 850 nm. As a result, little or no optical energy will couple from bus waveguide 504 to closed-loop waveguide 502 and little or no phase delay is induced on light signal 522. Light signals 522 and 520 combine constructively, therefore, and light signal 412 has a high intensity. While fluid 508 in detection region 404 comprises an analyte, therefore, light signal 412 will have a high intensity and output signal 416 will have a high voltage level.

FIG. 5D depicts a schematic diagram of details of a sensor element in accordance with a third alternative embodiment of the present invention. Sensor element 524 comprises closed-loop waveguide 502, bus waveguide 504, and bus waveguide 512. Closed-loop waveguide 502 and bus waveguide 504 collectively define waveguide resonator 526. Waveguide resonator 526 and bus waveguide 512 are arranged in an interferometer arrangement.

Operation of sensor element 524 is analogous to the operation of sensor element 516. The phase delay induced on light signal 522 is enhanced, however, by virtue of a second evanescent coupling region between closed-loop waveguide 502 and bus waveguide 504.

Figure 5E:
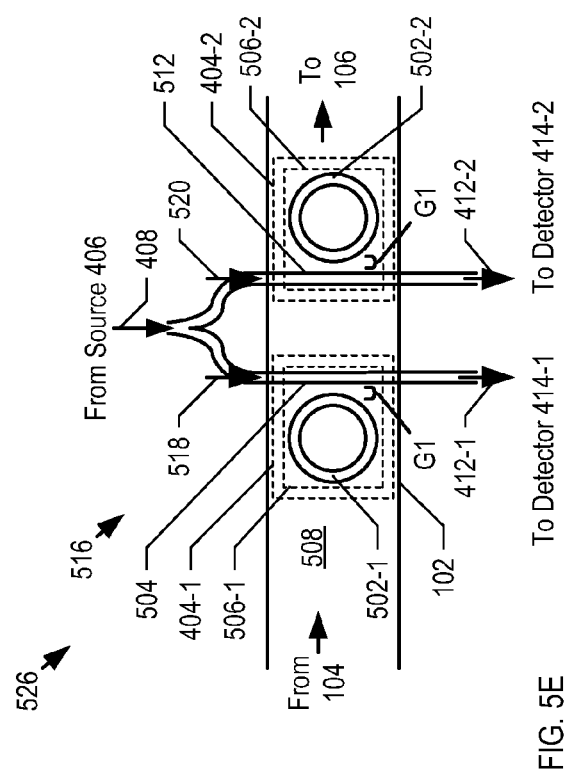
FIG. 5E depicts a schematic diagram of details of a sensor element in accordance with a fourth alternative embodiment of the present invention.

FIG. 5E depicts a schematic diagram of details of a sensor element in accordance with a fourth alternative embodiment of the present invention. Sensor element 526 comprises closed-loop waveguides 502-1 and 502-2, bus waveguide 504, and bus waveguide 512. Closed-loop waveguide 502 and bus waveguide 504 collectively define waveguide resonator 506-1. Closed-loop waveguide 502-2 and bus waveguide 512 collectively define waveguide resonator 506-2. Each of waveguide resonators 506-1 and 506-2 is analogous to waveguide resonator 506. Collectively, waveguide resonators 506-1 and 506-2 provide a differential signal that enables detection of a difference in the presence of analyte in detection regions 404-1 and 404-2.

Sensor element 526 enables detection of the presence of an analyte with spatial and/or temporal separation. In operation, as a charge of sample solution in fluid 508 flows from source reservoir 104 to destination reservoir 106, an analyte will first be detected at waveguide resonator 506-1. As with waveguide resonator 506, the arrival of an analyte in detection region 404-1 results in a change in the intensity of light signal 412-1. In similar fashion, as the analyte arrives at detection region 404-2, the intensity of light signal 412-2 changes.

By virtue of its multiple detection regions, sensor element 526 can provide:
 i. improved immunity to environmental noise (e.g., temperature changes, etc.); or
 ii. improved immunity to laser noise; or
 iii. a differential signal output based on the relative presence of analyte in detection regions 404-1 and 404-2; or
 iv. an indication of the flow rate of an analyte; or
 v. any combination of i, ii, iii, and iv.

In some applications, for example chemical lab-on-a-chip and micro-reactor applications, it can be advantageous to differentiate the presence of analyte in two or more regions that are physically close to one another. In addition to enabling such differentiation, sensor element 526 enables detection of rate of flow, progression through a microfluidic system, and detection of relative concentration.

In addition, in some applications, background noise from environmental changes or spurious noise associated with source 406 may degrade the signal-to-noise ratio of the output of the sensor element. Since each waveguide resonator included in sensor element 526 receives light from the same source and is subject to the same environmental conditions, the deleterious impact of such noise can be mitigated.

Although sensor element 526 comprises two waveguide resonators, it will be clear to one skilled in the art, after reading this specification, how to make and use alternative embodiments of the present invention wherein a sensor element comprises any number of waveguide resonators and detection regions.

In some embodiments, light signals 412-1 and 412-2 are combined into a signal light signal 412. In some embodiments, the intensity of this combined light signal 412 is dependent upon the relative phase of light signals 412-1 and 412-2.

A time differential between the arrival of analyte in detection regions 404-1 and 404-2 can be used, for example, as an indicator of analyte flow rate, monitor reaction rate, signal the presence of two reactants, and the like.

Figure 7:
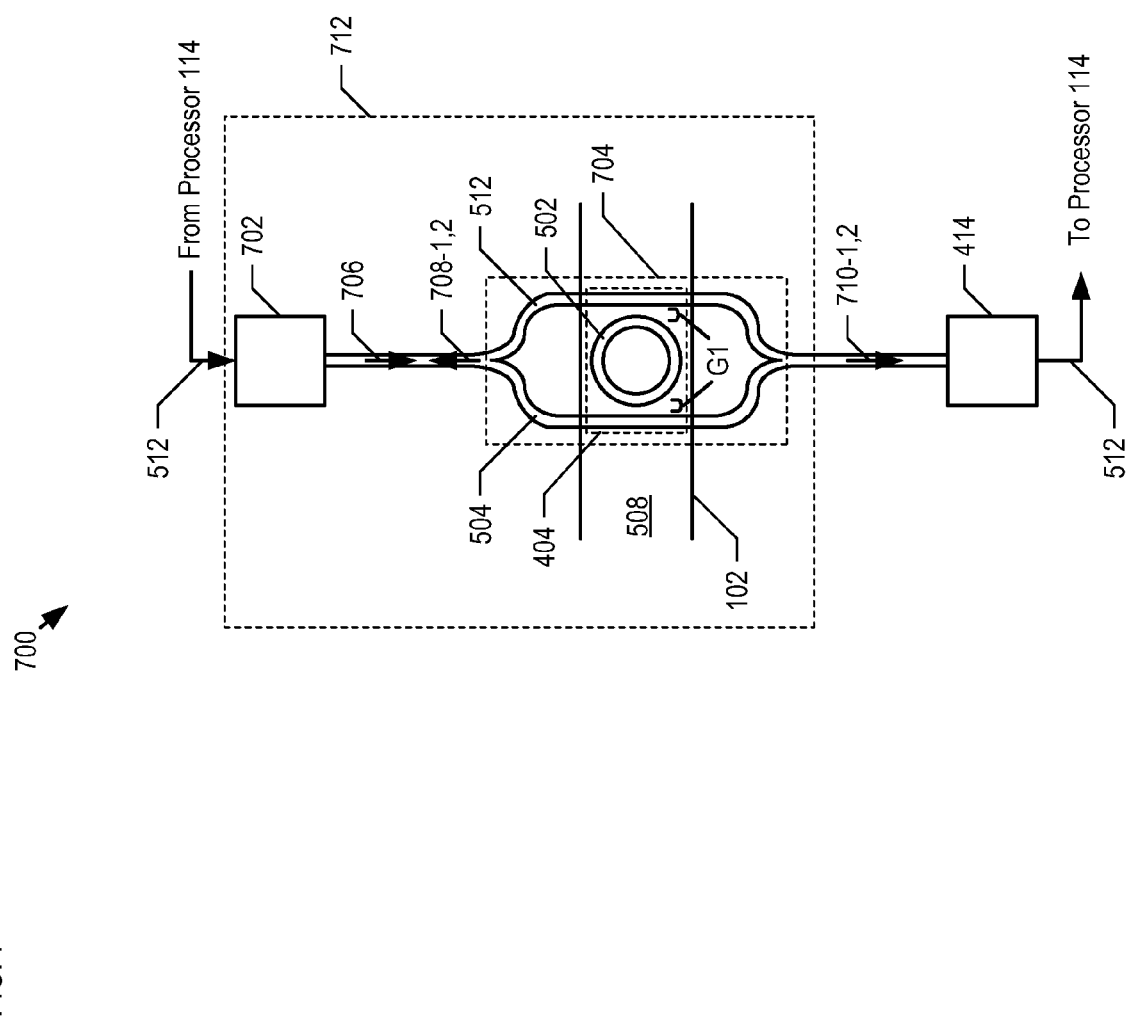
FIG. 7 depicts a schematic diagram of details of a sensor in accordance with a fifth alternative embodiment of the present invention.

FIG. 7 depicts a schematic diagram of details of a sensor in accordance with a fifth alternative embodiment of the present invention. Sensor 700 comprises laser 702, waveguide resonator mirror 704, and detector 414. Laser 702 and mirror 704 collectively define external cavity laser 712.

Laser 702 is a semiconductor laser that emits light having a spectral width that surrounds a center wavelength of approximately 833 nm. Laser 702 is analogous to source 406, however the center wavelength of laser 702 can be tuned over a tuning range of several tens of nanometers. It will be clear to those skilled in the art how to make and use laser 702. In some embodiments, laser 702 comprises a VCSEL. It should be noted that the emission wavelength of 833 nm is merely exemplary. It will be clear to one skilled in the art that the present invention is wavelength-independent and that any suitable laser can be used for laser 702; therefore, laser 702 can emit light at any wavelength consistent with laser technology.

Waveguide resonator mirror 704 (hereinafter referred to as mirror 704) comprises closed-loop waveguide 502 and bus waveguides 504 and 512, each of which are separated from closed-loop waveguide by gap G1. Mirror 704 is dimensioned and arranged to selectively return a spectral component to laser 702, wherein the optical resonance of mirror 704 determines the wavelength of the spectral component. Specifically, mirror 704 is dimensioned and arranged to selectively return a spectral component having a wavelength of 833 nm to laser 702 when fluid 508 in detection region 404 is analyte-free.

Figure 8:
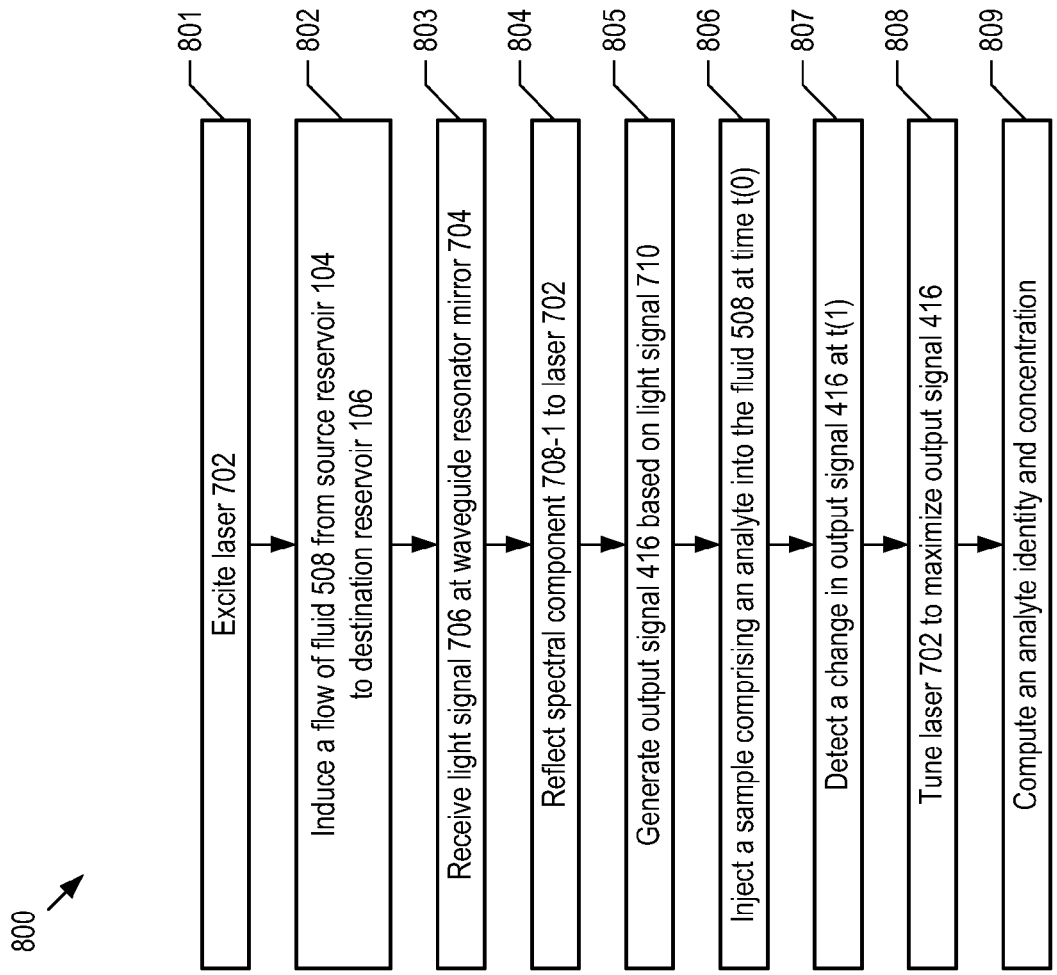
FIG. 8 depicts a method for detecting an analyte and computing the concentration of the analyte in a fluid in accordance with the fifth alternative embodiment of the present invention.

FIG. 8 depicts a method for detecting an analyte and computing the concentration of the analyte in a fluid in accordance with the fifth alternative embodiment of the present invention.

Figure 9:
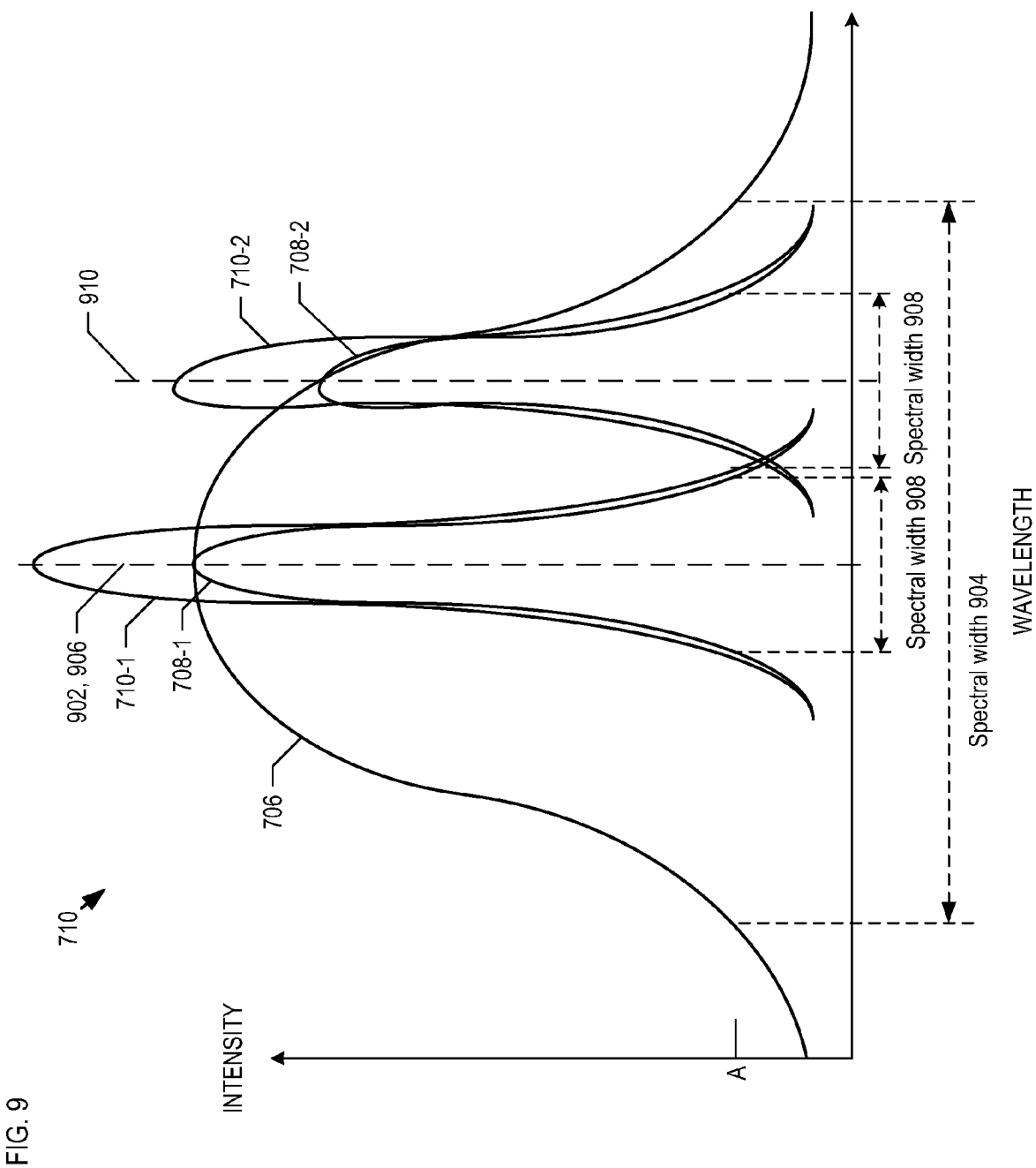
FIG. 9 depicts a plot of details of the optical response of an external cavity laser in accordance with the fifth alternative embodiment of the present invention.

Method 800 is described herein with continuing reference to FIGS. 4 and 7 and additional reference to FIG. 9. FIG. 9 depicts a plot of details of the optical response of an external cavity laser in accordance with the fifth alternative embodiment of the present invention.

Method 800 begins with operation 801, wherein laser 702 is electrically excited and emits light signal 706 having center wavelength 902 and spectral width 904.

At operation 802, flow channel 102 is filled with fluid 508, which comprises a pure buffer solution, typically a saline solution. Processor 114 then applies a high voltage between source reservoir 104 and destination reservoir 106 to induce a flow of fluid 508 between them. In some embodiments, the flow of fluid 508 is induced by another means, such as pressure, capillary action, or siphoning.

At operation 803, mirror 704 receives light signal 706.

At operation 804, mirror 704 selectively reflects spectral component 708-1 back to laser 702. When spectral component 708-1 is coupled into the laser cavity of laser 702, the gain of the laser cavity is enhanced for wavelengths contained in spectral component 708-1. In addition, emission by laser 702 of photons having wavelengths not contained in spectral component 708-1 is suppressed after a brief period of time. As a result, light signal 710-1 quickly becomes an amplified version of spectral component 708-1, matching the center wavelength 906 and spectral width 908 of spectral component 708-1.

At operation 805, detector 414 receives light signal 710-1 and generates output signal 416.

At operation 806, processor 114 applies a voltage pulse between sample inlet 110 and sample outlet 112. This applied voltage induces a charge of sample solution to be injected into fluid 508 at mixing region 118, where it mixes with the buffer solution. The charge of sample solution is injected into fluid 508 at time t(0). The sample solution comprises a mixture of a first analyte and a second analyte.

In similar fashion to method 300, described above and with respect to FIG. 3, as fluid 508 flows from source reservoir 104 to destination reservoir 106, it carries the charge of sample solution along flow channel 102 for distance d2 (i.e., from mixing region 118 to detection region 404). As the charge of sample solution moves along distance d2, it disassociates into its constituent parts of the first analyte and second analyte.

Each analyte moves along flow channel 102 at a rate that is a function of its unique electrophoretic mobility.

At time t(1), the first analyte reaches detection region 404 and the refractive index of fluid 508 in detection region 404 changes based on the concentration of analyte in the fluid. As the refractive index of fluid 508 changes, so does the wavelength of the spectral component reflected by mirror 704 to laser 702. As a result, the center wavelength of the selectively reflected spectral component shifts from a wavelength of 906 to a wavelength of 910, wherein the difference between these wavelengths is based on the concentration of analyte in detection region 404. This shift in the center wavelength of the reflected spectral component causes a commensurate shift in the center wavelength of the light output by external cavity laser 712 (i.e., light signal 710-1 shifts to light signal 710-2).

When light signal 710-1 shifts to light signal 710-2, its emission peak is no longer aligned with the peak of the emission spectrum of laser 702. As a result, the intensity of light signal 710-2 is lower than the intensity of light signal 710-1. This reduction in intensity induces a commensurate drop in the voltage level of output signal 416 at time t(1).

At operation 807, processor 114 detects the voltage drop in output signal 416 at time t(1).

At operation 808, processor 114 tunes laser 702 to maximize the intensity of light signal 710-2, and thereby maximize output signal 416. In some embodiments, processor tunes laser 702 by controlling the current with which the laser is driven. In some embodiments, processor 114 controls a tunable filter on the output of laser 702.

At operation 809, processor 114 derives an identity for the first analyte based on the difference between t(1) and t(0). In addition, processor 114 derives a concentration level for the first analyte based on the amount of wavelength tuning required to maximize the intensity of light signal 710-2.

As the first analyte dissipates from detection region 404, light signal 710-2 shifts back to light signal 710-1.

Operations 807 through 809 are repeated for each analyte contained in the sample injected into fluid 508 at time t(0).

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A sensor comprising:
    a substrate comprising a flow channel for conveying a fluid, wherein the flow channel comprises a first region and a second region that are separated by a first distance, and wherein the flow channel is dimensioned and arranged to enable flow of the fluid from the second region to the first region;
    the second region, the second region being dimensioned and arranged to enable injection of a sample containing a first analyte into the fluid at the second region;
    a first optically resonant element that is located within the first region, wherein the first optically resonant element is optically resonant for a first spectral component when the fluid in the first region has a first refractive index, and wherein the first optically resonant element is optically resonant for a second spectral component when the fluid in the first region has a second refractive index; and
    a processor, the processor operable to (1) induce injection of the sample into the fluid at a first time, (2) detect a change in the resonance of the first optically resonant element at a second time, and (3) compute a time differential between the first time and the second time; wherein the refractive index of the fluid is based on the presence of the first analyte.

2. The sensor of claim 1 wherein the processor is further dimensioned and arranged to (4) determine a property of the first analyte based on the time differential and the first distance.

3. The sensor of claim 1 wherein the first optically resonant element is selected from the group consisting of a disc resonator and a ring resonator.

4. The sensor of claim 1 further comprising a first bus waveguide and a second bus waveguide, wherein the first spectral component couples between the first bus waveguide and the second bus waveguide when the fluid in the first region has the first refractive index, and wherein the second spectral component couples between the first bus waveguide and the second bus waveguide when the fluid in the first region has the second refractive index.

5. The sensor of claim 1 further comprising:
    a first bus waveguide, wherein the first bus waveguide and the first optically resonant element collectively define a first waveguide resonator;
    a second bus waveguide; and
    an input port for distributing the first spectral component into a first light signal in the first bus waveguide and a second light signal in the second bus waveguide;
    wherein the first optically resonant element induces a phase change on the first light signal when the fluid in the first region has the first refractive index.

6. The sensor of claim 5 further comprising an output port for combining the first light signal and the second light signal, wherein the first waveguide resonator interposes the input port and the output port.

7. The sensor of claim 1 further comprising:
    a second optically resonant element; and
    a third region, wherein the flow channel comprises the third region, and wherein the second optically resonant element is located within the third region;
    wherein the second optically resonant element is optically resonant for the first spectral component when the fluid in the third region has the first refractive index, and wherein the second optically resonant element is optically resonant for the second spectral component when the fluid in the third region has the second refractive index.

8. A sensor comprising:
    a substrate comprising a flow channel for conveying a fluid, wherein the flow channel comprises a first region and a second region that are separated by a first distance, and wherein the flow channel is dimensioned and arranged to enable flow of the fluid from the second region to the first region;
    the second region, the second region being dimensioned and arranged to enable injection of a sample containing a first analyte into the fluid at the second region, wherein the refractive index of the fluid is based on the presence of the first analyte;
    a first optically resonant element that is located within the first region, wherein the first optically resonant element is optically resonant for a first spectral component when the fluid in the first region has a first refractive index, and wherein the first optically resonant element is optically resonant for a second spectral component when the fluid in the first region has a second refractive index;
    a first bus waveguide and a second bus waveguide, wherein the first bus waveguide, second bus waveguide, and first optically resonant element collectively define a first waveguide resonator; and an input port, wherein the input port, first bus waveguide and second bus waveguide are optically coupled;

wherein the first waveguide resonator is dimensioned and arranged to return the first spectral component to the input port when the fluid in the first region has the first index of refraction.

9. The sensor of claim 8 further comprising:

a detector, the detector being optically coupled with the input port, and the detector being dimensioned and arranged to provide a detector signal that is based on the intensity of one of the first spectral component and the second spectral component at the input port; and a processor, the processor operable to (1) induce injection of the sample into the first fluid at a first time, (2) detect a change in the detector signal at a second time, and (3) compute a time differential between the first time and the second time.

10. The sensor of claim 8 further comprising:

a second optically resonant element; and a third region, wherein the flow channel comprises the third region, and wherein the second optically resonant element is located within the third region;

wherein the second optically resonant element is optically resonant for the first spectral component when the fluid in the third region has the first refractive index, and wherein the second optically resonant element is optically resonant for the second spectral component when the fluid in the third region has the second refractive index.

11. The sensor of claim 10 wherein the processor is further operable to detect a change in the resonance of the second optically resonant element.

12. A sensor for detecting an analyte in a fluid, the sensor comprising:

a substrate comprising a flow channel dimensioned and arranged to induce a flow of the fluid between a first region and a second region;

an input port;

a first waveguide resonator comprising a first optically resonant element, a first bus waveguide, and a second bus waveguide, wherein the first optically resonant element is located within the first region, and wherein the first optically resonant element and the fluid are optically coupled at the first region; and a sample inlet for injecting a sample containing the analyte into the first fluid at the second region;

wherein the input port, first bus waveguide, and second bus waveguide are optically coupled, and wherein the first waveguide resonator is dimensioned and arranged to reflect a first spectral component to the input port when the fluid in the first region is analyte-free and a second spectral component to the input port when the fluid in the first region comprises the analyte.

13. The sensor of claim 12 wherein the first optically resonant element comprises a closed-loop waveguide that comprises a waveguide core having an inner core of stoichiometric silicon oxide ($SiO_2$), an outer core of stoichiometric silicon nitride ($Si_3N_4$), and a cladding that comprises the fluid in the first region.

14. The sensor of claim 12 further comprising a second waveguide resonator, wherein the second waveguide resonator comprises a second optically resonant element and a second bus waveguide;

wherein the flow channel comprises a third region, and wherein the second optically resonant element is located within the third region, and wherein the second optically resonant element and the fluid are optically coupled at the third region; and wherein the second waveguide resonator is dimensioned and arranged to receive a third light signal and provide a fourth light signal that is based on the third light signal, and further wherein the fourth light signal has a third intensity when the fluid is analyte-free and a fourth intensity when the fluid comprises the analyte.

15. The sensor of claim 12 further comprising:

a detector, the detector being optically coupled with the input port, and the detector being dimensioned and arranged to provide a detector signal that is based on the intensity of one of the first spectral component and the second spectral component at the input port; and a processor, the processor operable to (1) induce injection of the sample into the first fluid at a first time, (2) detect a change in the detector signal at a second time, and (3) compute a time differential between the first time and the second time.

16. A method for detecting an analyte in a fluid comprising:

providing a first waveguide resonator, wherein the first waveguide resonator comprises a first optically resonant element that is located within a first region of a flow channel for conveying the fluid, and wherein the first optically resonant element and the fluid are optically coupled at the first region such that the first optically resonant element is optically resonant at a first wavelength when the fluid in the first region is analyte-free and optically resonant at a second wavelength when the fluid in the first region comprises the analyte;

adding a sample comprising the analyte to the fluid at a first time, wherein the sample is added at a second region of the flow channel;

inducing a flow of the fluid from the second region to the first region;

receiving a first light signal from the first waveguide resonator, wherein the first light signal has a first intensity when the fluid in the first region is analyte-free and a second intensity when the fluid in the first region comprises an analyte; and computing a time differential between the first time and a second time, wherein the second time is based on a change in the intensity of the second signal.

17. The method of claim 16 further comprising:

computing a difference between the first wavelength and the second wavelength; and computing a concentration of analyte in the fluid at the first region based on the difference between the first wavelength and the second wavelength.

18. The method of claim 16 further comprising determining a property of the analyte based on (1) the time differential and (2) the separation between the second region and the first region.

19. The method of claim 16 further comprising:

transmitting a third light signal to a second waveguide resonator that comprises a second optically resonant element that is located within a third region of the flow channel, wherein the second optically resonant element and the fluid are optically coupled at the third region; and receiving a fourth light signal from the second waveguide resonator, wherein the fourth light signal has a third intensity when the fluid in the third region is analyte-free and a fourth intensity when the fluid in the third region comprises the analyte.

20. The method of claim 19 further comprising:
determining a property of the analyte based on (1) the time differential and (2) a separation between the first region and the second region.

21. A method for detecting an analyte in a fluid comprising:
providing a first waveguide resonator, wherein the first waveguide resonator comprises a first bus waveguide, a second bus waveguide, and a first optically resonant element that is located within a first region of a flow channel for conveying a fluid, and wherein the first optically resonant element and the fluid are optically coupled at the first region such that the first optically resonant element is optically resonant at a first wavelength when the fluid in the first region is analyte-free and optically resonant at a second wavelength when the fluid in the first region comprises an analyte;
distributing an input light signal into a first light signal and a second light signal, wherein the first bus waveguide conveys the first light signal, and wherein the second bus waveguide conveys the second light signal;
adding a sample comprising the analyte to the fluid at a first time, wherein the sample is added at a second region of the flow channel;
inducing a flow of the fluid from the second region to the first region;
receiving the first light signal at the first waveguide resonator;
receiving a third light signal from the first waveguide resonator, wherein the third light signal has a phase that is based on the presence of the analyte in the first region;
coupling the second light signal and the third light signal at an output port, wherein the first bus waveguide and second bus waveguide are optically coupled at the output port; and
generating an output light signal whose intensity is based on the relative phases of the second signal and the third signal at the output port; and
computing a time differential between the first time and a second time that is based on a change in the intensity of the output light signal.

22. The method of claim 21 further comprising determining a property of the analyte based on (1) the time differential and (2) a separation between the first region and the second region.

* * * * *